| United States Patent [19] | [11] | 4,323,479 |
|---|---|---|
| Batalin et al. | [45] | Apr. 6, 1982 |

[54] CATALYST FOR DECOMPOSITION OF 1,3-DIOXANES

[76] Inventors: Oleg E. Batalin, ulitsa Ordzhonikidze, 45, kv. 85; Arkady S. Dykman, ulitsa Leni Golikova, 37, korpus 4, kv. 15; Alexandr I. Osadchenko, ulitsa Sofiiskaya, 23, korpus 2, kv. 174; Galina F. Balkhanova, ulitsa Telmana, 48, korpus 3, kv. 60, all of Leningrad; Izrail M. Belgorodsky, Molodezhny bulvar, 50, kv. 25, Tolyatti; Vladimir I. Nevstruev, ulitsa Karla Marxa, 52, kv. 31, Tolyatti; Valery A. Radionov, ulitsa Matrosova, 30, kv. 180, Tolyatti; Eduard A. Tulchinsky, ulitsa Ushakova, 46, kv. 12, Tolyatti; Valentin M. Belyaev, prospekt Lenina, 32, kv. 20, Volzhsky; Jury I. Smolin, prospekt Lenina, 97, kv. 494, Volzhsky; Mark I. Breiman, ulitsa Chaikovskogo, 17, kv. 12, Volzhsky; Vitaly V. Orlyansky, ulitsa Pionerskaya, 8"a", kv. 4, Volzhsky; Nikolai Y. Zhirnov, ulitsa Sovetskaya, 59, kv. 35, Volzhsky; Nikolai V. Galibin, ulitsa Pushkina, 122, kv. 49, Volzhsky; Andrian P. Troitsky, ulitsa Miklukho-Maklaya, 65, korpus 2, kv. 46, Moscow; Vladimir V. Kovalenko, ulitsa Tsiolkovskogo, 7/2, kv. 38, Voronezh, all of U.S.S.R.

[21] Appl. No.: 172,635

[22] Filed: Jul. 25, 1980

[51] Int. Cl.$^3$ .............................................. B01J 21/02
[52] U.S. Cl. .................................................... 252/432
[58] Field of Search ........................................ 252/432

[56] References Cited

U.S. PATENT DOCUMENTS 2,834,738  5/1958  Vincent .............................. 252/432
4,177,158  12/1979  Blue ................................ 252/432 X

OTHER PUBLICATIONS

Kinetics and Catalysis, 1960, vol. 1, issue 2, pp. 247–256.
Khimia i Khimicheskaja technologia, vol. 7, No. 5, pp. 801–805.

*Primary Examiner*—Delbert E. Gantz
*Assistant Examiner*—William G. Wright
*Attorney, Agent, or Firm*—Steinberg & Raskin

[57] ABSTRACT

A catalyst for decomposition of 1,3-dioxanes, comprising calcium oxide, phosphorus pentoxide, chlorine, water and boron oxide, the ratio of the components as expressed in mass percent being as follows:
calcium oxide: 48.5 to 53.5
phosphorus pentoxide: 42.5 to 46.5
chlorine: 0.05 to 1.0
boron oxide; 0.005 to 3.0
the balance being water.

7 Claims, No Drawings

CATALYST FOR DECOMPOSITION OF 1,3-DIOXANES

FIELD OF THE INVENTION

The present invention relates to the production of catalysts which can be used, for example, in the manufacture of isoprene from isobutylene and formaldehyde, as well as in alcohol dehydration reactions, and more particularly, to a catalyst used for the decomposition of 1,3-dioxanes, in particular, 4,4-dimethyl-1,3-dioxane (hereinafter referred to as DMD) into isoprene.

BACKGROUND OF THE INVENTION

Catalysts comprising from 54.2 to 56.3 mass percent of calcium oxide, from 42.8 to 45.7 mass percent of phosphorus pentoxide, the balance (up to 100%) being water (see, for example, "Kinetics and Catalysis", 1960, volume 1, issue 2, pp. 247–256) are widely used at the present time.

In reactions of decomposition of 1,3-dioxanes, the catalysts of the above-mentioned composition possess a low activity resulting in a low space velocity of the raw material feed equal to 0.5 to 0.7 $h^{-1}$ and a high operating temperature of the catalyst that is equal to approximately 370° to 390° C.

The activity of catalysts is known to depend upon the acidity thereof which is determined by the number and efficiency of the active centres and can be characterized by the degree of decomposition of 1,3-dioxanes under similar operating conditions.

The degree of decomposition of 1,3-dioxanes is defined as the ratio of the amount of 1,3-dioxanes converted, to that of 1,3-dioxanes used, both being expressed in moles. The level of decomposition is expressed in percent.

The selectivity of the above-mentioned catalysts is also not high and lies at a level of 68 to 75 mole %.

The selectivity is defined as the ratio of the amounts in moles of isoprene formed to the amount in moles of 1,3-dioxane converted, expressed in percent.

Selectivity is quantitatively dependent upon catalyst composition and structure, as well as upon the process conditions under which the catalyst operates.

Increased selectivity will lead to reduced stockfeed consumption rates per unit of finished product, thus per ton of isoprene. A relatively low selectivity of the catalyst would result in high feedstock consumption rates in the isoprene production, varying between ca. 2.10 and 2.25 kg of 1,3-dioxanes per 1 kg of isoprene.

Furthermore, the above-mentioned catalysts feature a higher coke deposition ability of 3.0 to 5.0 mole %. Coke deposition is defined as the ratio of the amount in moles of coke deposited to the amount in moles of 1,3-dioxane converted, expressed in percent. Increased coke deposition leads to a decrease in the selectivity of the 1,3-dioxane decomposition process and increases the unproductive waste of energy used for the catalyst recovery process that involves the burning-out of the deposited coke by a steam-air mixture at a temperature of 400° to 500° C.

Also known in the prior art are catalysts comprising 12.8 mass percent of cadmium oxide, 40.1 mass percent of calcium oxide, 40.0 mass percent of phosphorus pentoxide, and water up to 100 mass percent (see, for example, "Izvestia visshich utchebnich zavedenij", Chimija i chimitcheskaja technologija, vol. 7, No. 5, pp. 801–805).

The catalysts of the above composition show a low activity and a comparatively short life of 300 h.

The catalyst life depends upon many factors including catalyst composition and structure, catalyst activity, operating temperature, and coke deposition.

Furthermore, the catalysts of said type show a low selectivity of 78 to 80 mole %. The known catalysts feature also a low efficiency within 0.20 to 0.25 t/h of isoprene per cubic meter of the catalyst. The efficiency of the catalyst depends upon its activity and selectivity, as well as upon the space velocity of raw material feed.

In spite of the advantages of the known catalysts, no commerical process has been so far developed for the decomposition of 1,3-dioxanes with the use of such catalysts, since there is no catalyst as yet devised which would exhibit the selectivity and stability such as to justify a commercial process with a high yield of the final product.

SUMMARY OF THE INVENTION

It is an object of the present invention to provide a catalyst for decomposition of 1,3-dioxanes, that possesses an enhanced activity at low operating temperatures that are lower than or equal to 300° C.

Another object of the present invention is to provide a high-efficiency catalyst for decomposition of 1,3-dioxanes.

A further object of the present invention is to provide a high-selectivity catalyst for decomposition of 1,3-dioxanes.

A still further object of the present invention is to provide a catalyst for decomposition of 1,3-dioxanes with a longer life and low coke deposition during the service thereof.

With these and other objects in view, there is provided a catalyst for decomposition of 1,3-dioxanes, comprising calcium oxide, phosphorus pentoxide, chlorine, and water, which catalyst, according to the invention, further comprises boron oxide, the ratio of the components expressed in mass percent being as follows:

calcium oxide: 48.50 to 53.50
phosphorus pentoxide: 42.50 to 46.50
chlorine: 0.05 to 1.00
boron oxide: 0.005 to 3.000
the balance being water.

The catalyst for decomposition of 1,3-dioxanes of the proposed composition shows a high activity at low operating temperatures as compared with the known prior art catalysts, that is evidenced by an approximately 40% increase in the degree of 1,3-dioxane decomposition at a temperature of 280° C. Selectivity of the 1,3-dioxane decomposition using the proposed catalyst is higher by at least 12 mole % than that with the use of the known catalysts and lies within the limits of from 87 to 88 mole %.

The catalyst life is approximately six times that of the known catalysts.

It is advisable that the catalyst for decomposition of 1,3-dioxanes contains 0.02 to 0.3 mass percent of boron oxide.

Such content of boron oxide at the component ratio stated above allows improvement in the stability of the catalyst, thus resulting in a practically constant degree of decomposition during 100 operating hours.

It is also advisable that the chlorine content of the proposed catalyst be 0.20 to 0.30 mass percent.

The specified content of chlorine allows coke deposition to be reduced down to 1 mole % or below.

Used as starting reactants are solutions of calcium salts, e.g. calcium chloride, and phosphoric acid salts, e.g. diammonium phosphate, disodium phosphate, etc. A suitable amount of aqueous ammonia is added to the phosphate solution prior to reacting it with the calcium salt solution to control the pH of the medium.

The solution of the calcium salt and of the phosphate are gradually poured into a vessel fitted with a stirrer, while stirring the slurry continuously being formed. The reaction is carried out with the calcium salts and phosphoric acid salts taken in a molar ratio of 1.5:1. However the reaction is realizable with the starting reactants having a molar ratio anywhere within the range of 1.5:1 to 5.0:1, preferably 2.5:1. In this case, the reaction mixture is treated with a phosphoric acid solution to pH of from 5.0 to 7.0 and preferably of 5.5 to 6.0.

The above ranges of the calcium-salts-to-phosphoric acid salts ratios and of the pH values of the reaction mixture provide for the production of a calcium phosphate catalyst with the desired structure and composition.

The resulting precipitate is separated by filtration or any other conventional technique, washed with distilled water to remove calcium salt anions, shaped into granules by a conventional technique, and dried at a temperature of 110° to 140° C., thus obtaining a raw calcium phosphate that is then loaded into a reactor.

The reactor is a quartz tube of 20 to 26 mm in diameter. The tube is placed into an electrically heated furnace.

Boron is introduced into the raw calcium phosphate in the course of the thermal treatment at 400° to 600° C. using steam mixed with either boric acid or a mixture of boric and phosphoric acids. Boric acid is added to steam in an amount of 0.01 to 0.8 mass percent, preferably of 0.02 mass percent. In the case where thermal treatment of the catalyst is accomplished in the presence of the mixture of boric and phosphoric acids; the content of the boric acid in the steam is 0.001 to 0.02% mass percent and the phosphoric acid content is 0.0015 to 0.03% mass percent while the preferable contents are 0.002 mass percent for boric acid and 0.003 mass percent for phosphoric acid.

In the course of the treatment the molar ratio of boric acid and phosphoric acid is maintained in the range of 0.1:1 to 10:1, preferably 1:1.

Duration of the treatment is 2 to 50 hours, preferably 20 to 30 hours.

The thermal treatment can be also performed with steam mixed with air or an inert gas such as nitrogen, argon, etc.

In the course of the thermal treatment steam is supplied at a space velocity of 0.5 to 2.5 $h^{-1}$, preferably 1.0 to 2.0 $h^{-1}$.

If the calcium phosphate catalyst is produced without any treatment of the reaction mixture by a phosphoric acid solution, thermal treatment is preferably performed at a temperature of 400° C.

In the case where the process to prepare the calcium phosphate catalyst includes the stage of the slurry treatment by phosphoric acid to pH of from 5.0 to 7.0, thermal treatment is preferably carried out at a temperature of 450° C.

The catalyst thus obtained comprises, in % by mass: 48.50 to 53.50 of calcium oxide, 42.50 to 46.50 of phosphorus pentoxide, 0.05 to 1.00 of chlorine, 0.005 to 3.0 of boron oxide, the balance being water. It is preferable that the calcium oxide-to-phosphorus pentoxide molar ratio be at a level of 2.80 to 2.95. As to the activity, selectivity and stability, the best results are provided by a catalyst comprising 0.02 to 0.30 mass percent of boron oxide. The DMD conversion is at a level of 90% and remains practically constant during 100 operating hours, while selectivity is 87.0 to 88.0 mole %.

As to the coke deposition, the best results are achieved with the chlorine content of 0.20 to 0.30 mass percent. The coke deposition is at a level not exceeding 1 mole %.

The invention will be further described with reference to the following illustrative Examples.

EXAMPLE 1

The initial calcium phosphate was treated with steam containing 0.001 mass percent of boric acid and 0.0015 mass percent of phosphoric acid added thereto, at a temperature of 400° C. for 24 hours. The catalyst thus produced contained following components expressed in mass percent: calcium oxide, 48.50; phosphorus pentoxide, 43.00; chlorine, 0.26; boron oxide, 0.007; the balance being water. The catalyst was tested in a DMD decomposition reaction in a steam atmosphere. The DMD decomposition reaction was carried out at an average temperature of 280° C. and the atmospheric pressure for 100 h. 24 $cm^3$ of the catalyst were loaded into a reactor which was a quartz tube 20 to 26 mm in diameter. The reactor was placed into an electric furnace. DMD was fed in at a rate of 24 $cm^3$ per hour, while water was fed in at a rate of 48 $cm^3$ per hour, which gave space velocity of DMD feed equal to 1.0 $h^{-1}$ and a DMD-to-steam dilution ratio of 1:2. The contact cycle of 2 hours duration was followed by a regeneration cycle involving burning-out of the coke deposited. The regeneration cycle was carried out using a steam-air mixture at a temperature of 425° C., supplying 48 $cm^3$ of water and 16,800 $cm^3$ of air. The catalyst was analyzed during the gas-liquid chromatography technique. The amount of coke deposited was determined by a conventional method. The test results are given in Table 1.

EXAMPLE 2

The starting calcium phosphate was treated with steam containing 0.020 mass percent of boric acid at a temperature of 600° C. for 24 hours. The catalyst thus produced was composed of the following components expressed in mass percent: calcium oxide, 53.50; phosphorus pentoxide, 46.06; chlorine, 0.25; boron oxide, 0.271; the balance being water.

The catalyst was test run as described in Example 1. The test results are given in Table 1.

EXAMPLE 3

The starting calcium phosphate was treated essentially as described in Example 1. The treatment temperature was 450° C. The concentration of boric acid was 0.002 mass percent, that of phosphoric acid, 0.0030 mass percent. The catalyst thus produced was composed of the following components expressed in mass percent: calcium oxide, 49.03; phosphorus pentoxide, 42.50; chlorine, 0.24; boron oxide, 0.039; the balance being water.

The catalyst was test run as described in Example 1. The test results are given hereinbelow in Table 1.

EXAMPLE 4

The starting calcium phosphate was treated essentially as described in Example 1. The treatment temperature was 475° C. The concentration of boric acid was 0.006 mass percent, that of phosphoric acid, 0.0090 mass percent. The catalyst thus produced was composed of the following components expressed in mass percent: calcium oxide, 51.63; phosphorus pentoxide, 46.50; chlorine, 0.22; boron oxide, 0.150; the balance being water.

The catalyst was test run as described in Example 1. The test results are given in Table 1.

EXAMPLE 5

The starting calcium phosphate was treated essentially as described in Example 2. The treatment temperature was 500° C.

The catalyst thus was composed of the following components expressed in mass percent: calcium oxide, 52.30; phosphorus pentoxide, 45.10; chlorine, 0.05; boron oxide, 0.232; the balance being water.

The catalyst was test run as described in Example 1. The test results are given in Table 1.

EXAMPLE 6

The starting calcium phosphate washed incompletely free of chlorine ions was treated essentially as described in Example 3. The catalyst thus produced was composed of the following components expressed in mass percent: calcium oxide, 51.31: phosphorus pentoxide, 44.61; chlorine, 1.00; boron oxide, 0.054; the balance being water. The catalyst was test run as described in Example 1. The test results are given in Table 1.

EXAMPLE 7

The starting calcium phosphate was treated essentially as described in Example 1. The treatment temperature was 450° C.

The catalyst thus produced was composed of the following components expressed in mass percent: calcium oxide 50.95; phosphorus pentoxide, 44.78; chlorine, 0.22; boron oxide, 0.005: the balance being water. The catalyst was test run as described in Example 1. The test results are given in Table 1.

EXAMPLE 8

The starting calcium phosphate was treated essentially as described in Example 2. The treatment temperature was 450° C. The concentration of boric acid was 0.800 mass percent.

The catalyst thus produced was composed of the following components expressed in percent by mass: calcium oxide, 51.42; phosphorus pentoxide, 44.88; chlorine, 0.24; boron oxide, 3.000; the balance being water.

The catalyst was test run as described in Example 1. The test results are given in Table 1.

EXAMPLE 9

The starting calcium phosphate was treated essentially as described in Example 3. The treatment temperature was 475° C. The catalyst thus produced was composed of the following components expressed in mass percent: calcium oxide, 51.05; phosphorus pentoxide, 44.71; chlorine, 0.30; boron oxide, 0.040; the balance being water. The catalyst was test run as described in Example 1. The test results are given in Table 1.

EXAMPLE 10

The starting calcium phosphate was treated essentially as described in Example 3. The treatment temperature was 450° C. The concentration of boric acid was 0.02 mass percent, that of phosphoric acid was 0.03 mass percent. The catalyst thus produced was composed of the following components expressed in mass percent: calcium oxide, 51.00; phosphorus pentoxide, 45.14; chlorine, 0.27; boron oxide, 0.300; the balance being water. The catalyst was test run as described in Example 1. The test results are given in Table 1.

EXAMPLE 11

The starting calcium phosphate was treated in the same manner as described in Example 3. The treatment duration was 30 hours. The catalyst thus produced was composed of the following components expressed in mass percent: calcium oxide, 49.53; phosphorus pentoxide, 43.23; chlorine, 0.20; boron oxide, 0.045; the balance being water. The catalyst was test run as described in Example 1. The test results are given in Table 1.

EXAMPLE 12

The starting calcium phosphate was treated in the same manner as described in Example 3. The treatment duration was 50 hours. The catalyst thus produced was composed of the following components expressed in mass percent: calcium oxide, 50.12; phosphorus pentoxide, 43.90; chlorine, 0.18; boron oxide, 0.059; the balance being water. The catalyst was test run as described in Example 1. The test results are given in Table 1.

Although the present invention has been described herein with reference to preferred typical embodiments thereof, it will be apparent to those skilled in the art that there may be minor modifications made in the preparation of the catalyst for decomposition of 1,3-dioxanes without departing from the spirit of the invention.

All such modifications and variations are contemplated to be embraced in the spirit and scope of the invention, as defined in the appended claims.

TABLE 1

Results of catalyst testing in DMD decomposition

Operating temperature: 280° C.
Space velocity of DMD feed: 1 h$^{-1}$ DMD-to-H$_2$O dilution ratio: 1:2

| Characteristics | Catalyst as per Example Nos. | | | | | | | | | | | |
|---|---|---|---|---|---|---|---|---|---|---|---|---|
| | 1 | | 2 | | 3 | | 4 | | 5 | | 6 | |
| Cycle Nos. | 1 | 50 | 1 | 50 | 1 | 50 | 1 | 50 | 1 | 50 | 1 | 50 |
| DMD conversion level, % | 90.0 | 89.4 | 83.2 | 79.5 | 90.1 | 89.9 | 90.2 | 89.9 | 86.0 | 82.4 | 90.4 | 90.1 |
| Selectivity, mole % | 87.2 | 87.6 | 87.5 | 87.9 | 87.6 | 88.0 | 87.6 | 88.0 | 87.5 | 87.8 | 87.0 | 87.5 |

TABLE 1-continued

Results of catalyst testing in DMD decomposition
Operating temperature: 280° C.
Space velocity of DMD feed:
1 h⁻¹ DMD-to-H₂O dilution ratio: 1:2

| Coke deposition mole % | 0.94 | 0.56 | 0.49 | 0.35 | 0.71 | 0.52 | 0.58 | 0.45 | 0.71 | 0.50 | 1.20 | 0.87 |
|---|---|---|---|---|---|---|---|---|---|---|---|---|

| Characteristics | Catalyst as per Example Nos. | | | | | | | | | | | |
|---|---|---|---|---|---|---|---|---|---|---|---|---|
| | 7 | | 8 | | 9 | | 10 | | 11 | | 12 | |
| Cycle Nos. | 1 | 50 | 1 | 50 | 1 | 50 | 1 | 50 | 1 | 50 | 1 | 50 |
| DMD conversion level, % | 89.8 | 89.2 | 90.2 | 86.3 | 90.0 | 89.7 | 90.1 | 86.3 | 90.1 | 89.8 | 90.0 | 89.8 |
| Selectivity, mole % | 87.4 | 87.7 | 87.2 | 87.6 | 87.7 | 88.0 | 87.4 | 87.7 | 87.7 | 87.9 | 87.5 | 87.7 |
| Coke deposition mole % | 0.81 | 0.55 | 1.00 | 0.69 | 0.60 | 0.49 | 0.96 | 0.62 | 0.67 | 0.50 | 0.63 | 0.47 |

What is claimed is:

1. A catalyst for the decomposition of 1,3-dioxanes, consisting essentially of calcium oxide, phosphorus pentoxide, chlorine, water and boron oxide, in the following ratio expressed in mass percent:
   calcium oxide: 48.5 to 53.5
   phosphorus pentoxide: 42.5 to 46.5
   chlorine: 0.05 to 1.0
   boron oxide: 0.005 to 3.0
   the balance being water.

2. A catalyst as defined in claim 1, wherein the mass percent of boron oxide is 0.02–0.3.

3. A catalyst as defined in claim 1, wherein the mass percent of chlorine is 0.2–00.3.

4. Method of producing the catalyst of claim 1, which comprises reacting a solution of calcium chloride with a solution of a phosphoric acid salt in a molar ratio of calcium salt to phosphoric acid salt between 1.5:1 and 5.0:1 at a pH of 5.0–7.0 to form calcium phosphate of the desired composition, separating the thus formed calcium phosphate from the reaction mass and subjecting the same to a thermal treatment at 400°–600° C. with steam containing boric acid in an amount sufficient to incorporate therein said amount of boron oxide.

5. Method according to claim 4 wherein said steam contains a mixture of boric and phosphoric acids.

6. Method according to claim 4 wherein said steam contains boric acid in an amount of 0.01 to 0.8 mass percent.

7. Method according to claim 5 wherein said steam contains 0.001 to 0.02 mass percent of boric acid and 0.0015 to 0.03 mass percent of phosphoric acid.

* * * * *